United States Patent [19]

Malen et al.

[11] 4,001,420
[45] Jan. 4, 1977

[54] THIAZOLYL BENZOIC ACID COMPOUNDS

[75] Inventors: Charles Malen, Fresnes; Pierre Desnoyers, Fontenay-aux-Roses, both of France

[73] Assignee: Science Union et Cie, Suresnes, France

[22] Filed: Apr. 25, 1974

[21] Appl. No.: 463,912

Related U.S. Application Data

[62] Division of Ser. No. 881,590, Dec. 2, 1969, Pat. No. 3,821,237.

[30] Foreign Application Priority Data

Dec. 12, 1968   United Kingdom ............ 59720/68

[52] U.S. Cl. .................................... 424/270
[51] Int. Cl.² ..................................... A61K 31/425
[58] Field of Search ................................. 424/270

[56] References Cited

UNITED STATES PATENTS

| 3,558,641 | 1/1971 | Sarett et al. | 260/295 |
| 3,676,451 | 7/1972 | Sarett et al. | 260/295 |

*Primary Examiner*—Frederick E. Waddell
*Attorney, Agent, or Firm*—Gordon W. Hueschen

[57] ABSTRACT m-(thiazol-4-yl) benzoic acids substituted in 2- and optionally 5-position of the thiazol ring by lower alkyl, phenylalkyl, phenyl, halo-phenyl, lower alkylphenyl or lower alkoxyphenyl, and on the phenyl ring of the benzoic acid moiety by halogen, hydroxyl, lower alkyl or lower alkoxy. These compounds possess fibrinolytic, platelet stickiness decreasing and antiulcer properties and have an impact on the immunological processes.

9 Claims, No Drawings

THIAZOLYL BENZOIC ACID COMPOUNDS

This is a division of application Ser. No. 881,590, filed Dec. 2, 1969, now issued as U.S. Pat. 3,821,237.

The present invention provides thiazolyl benzoic acid compounds of the general formula (I):

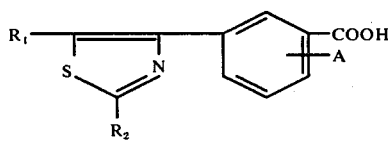

wherein:

$R_1$ and $R_2$ are selected from the group consisting of: a linear or branched lower alkyl chain containing 1 to 5 carbon atoms inclusive, a phenylalkyl radical, and a phenyl radical optionally substituted by one or more halogen atoms, lower alkyl or lower alkoxy radicals containing 1 to 5 carbon atoms inclusive and for $R_1$ a hydrogen atom, and A is selected from the group consisting of: a hydrogen atom, a halogen atom, a hydroxy radical and a lower alkyl or lower alkoxy radical containing 1 to 5 carbon atoms inclusive.

These compounds are new and may be prepared by a known method described by Hantzsch et al. Ann 294 1 (1888), by reacting an α-haloketone of the general formula (II):

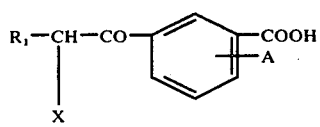

wherein $R_1$ and A have the meanings defined above and X represents a chlorine or bromine atom, with a thioamide of the general formula (III):

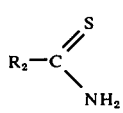

wherein $R_2$ has the meaning given above.

The compounds of general formula (I) may be converted into addition salts with mineral or organic bases, such, for example, as bases of alkaline metals, and secondary or tertiary amines, such as di- and triethylamines. These salts are also included in the present invention.

The following Examples illustrate the invention. Melting points are determined on a Kofler heater plate under the microscope (MK) or on a Kofler bank (KB).

EXAMPLE 1

2-hydroxy-5-(2-methyl thiazol-4-yl) benzoic acid

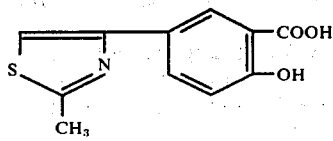

A solution of 53 g (0.2 mol) of 2-hydroxy-5-(α-bromoacetyl) benzoic acid in 250 ml of slightly warm ethanol was dropped, for 15 minutes, in a solution of 15 g (0.2 mol) of thioacetamide in 60 ml of ethanol, while stirring vigorously. The reaction was slightly exothermic, and a white product gradually precipitated. Stirring was maintained for one hour, then the reaction mixture was diluted with 500 ml of water. The precipitate was filtered off, washed with water and the product was recrystallized from ethanol. 40.6 g of 2-hydroxy 5-(2-methyl thiazol-4-yl) benzoic acid, M.P. (K.B.) 250°–253° C, were obtained (yield 83%). A second yield of product was obtained by concentration of the ethanolic mother liquors. 3.1 g (0.0425 mol) of diethylamine was added to a suspension of 10 g (0.0425 mol) of the acid prepared above in 50 ml of ethanol. The mixture was stirred for 30 minutes then concentrated to dryness. The residue was recrystallized from benzene. 10.3 g of diethylammonium 2-hydroxy-5-(2-methyl thiazol-4-yl) benzoate are obtained, M.P. (M.K.) 128°–132° C with progressive recrystallization and second M.P. 249°–250° C (yield 78 %).

Ovver its melting point, the diethylammonium salt gives diethylamine regenerating then the corresponding acid: the second melting point corresponds to the complete transformation in free acid.

EXAMPLES 2 – 14

The following compounds were prepared according to the method described in Example 1:

2. 2-hydroxy-5-(2-phenyl thiazol-4-yl) benzoic acid, M.P. (M.K.) 210°–211° C with sublimation (acetonitrile), starting from 2-hydroxy-5-(α-bromacetyl) benzoic acid and thiobenzamide.

3. 2-hydroxy-5-[2-(3,4-dimethoxyphenyl) thiazol-4-yl] benzoic acid monohydrate, M.P.(K.B.) 140° C then 218°–222° C (ethanol), starting from 2-hydroxy-5-(α-bromoacetyl) benzoic acid and thioveratramide.

4. 2-methoxy-5-(2-phenyl thiazol-4-yl) benzoic acid, M.P. (K.B.) 169°–170° C, starting from 2-methoxy-5-(α-bromoacetyl) benzoic acid and thiobenzamide.

5. Diethylammonium 2-methoxy-5-(2-methyl thiazol-4-yl) benzoate, instantaneous M.P. (K.B.) 130°–132° C (benzene), M.P. (K.B.) of the corresponding acid 157°–160° C, starting from 2-methoxy-5-(α-chloroacetyl) benzoic acid and thioacetamide.

6. Diethylammonium 3-(2-methyl thiazol-4-yl) benzoate, M.P. (K.B.) 135°–137° C, M.P. (K.B.) of the corresponding acid 194°–196° C, starting from 3-(α-bromoacetyl) benzoic acid and thioacetamide.

7. Diethylammonium 2-chloro-5-(2-methyl thiazol-4-yl) benzoate, M.P. (M.K.) 145°–150° C (benzene), M.P. (M.K.) of the corresponding acid 206°–209° C, starting from 2-chloro-5-(α-bromoacetyl) benzoic acid and thioacetamide.

8. 3-(2,5-dimethyl thiazol-4-yl) benzoic acid,
M.P. (M.K.) 150°–154° C (acetonitrile) starting from 3-(α-bromopropionyl) benzoic acid and thioacetamide.

9. 2-methoxy-5-(2-benzyl thiazol-4-yl) benzoic acid,
M.P. (M.K.) 136°–139° C, starting from 2-methoxy-5-(α-bromoacetyl) benzoic acid and phenylethane thioamide.

10. Diethylammonium 2-methyl-3-(2-isobutyl thiazol-4-yl) benzoate,
starting from 2-methyl-3-(α-bromoacetyl) benzoic acid and thioisovaleramide.

11. Diethylammonium 2-bromo-5-(2-ethyl-5-phenyl thiazol-4-yl) benzoate,
starting from 2-bromo-5-(phenyl α-bromoacetyl) benzoic acid and thiopropionamide.

12. Diethylammonium 3-(2-methyl-5-paratolyl thiazol-4-yl)-4-ethoxy benzoate,
starting from 3-(paratolyl α-bromoacetyl)-4-ethoxy benzoic acid and thioformamide.

13. 3-ethyl-5-(2-methyl-5-propyl thiazol-4-yl) benzoic acid,
starting from 3-ethyl-5-(α-bromovaleryl) benzoic acid and thioacetamide.

14. 3-(2-parachlorophenyl thiazol-4-yl) benzoic acid,
starting from 3-(α-bromoacetyl) benzoic acid and parachlorothiobenzamide.

The new compounds of thiazolyl benzoic acid and their physiologically tolerable salts of the present invention possess valuable pharmacological and therapeutic properties, especially with regard to fibrinolysis, platelet stickiness, ulcer and immunological processes.

Their toxicity is very weak and the $LD_{50}$ in mice varies from 187,5 mg/kg to >1000 mg/kg by intraperitoneal administration and from 1000 mg/kg to >2000 mg/kg by the oral route.

The fibrinolytic activity was studied by the method described by von Kaulla in Thromb. Diath. Haemorrhag. 5, 489–494 (1961). By administering intravenously to the rat 5 to 10 mg/kg of the new products, a decrease of 6 to 64 % of the euglobulin lysis time may be observed 10 to 30 minutes after the injection. By oral administration, 50 to 100 mg/kg provoked a decrease of 4 to 54 % of the euglobulin lysis time, after 1 to 3 hours.

Using the method of S. Wessler (J. Clin. Invest. 34, 647–651 (1955)), it can be observed that the compounds of the invention, at a dose of 50 mg/kg I.V., inhibit totally or partially the formation of thrombus in the vena jugularis of the rabbit, provoked by injection of a heterologous human or rat serum, showing thus an activity of the products on fibrinolysis and immunological conditions. It is to be noted that in this assay human or rat serum induces a thrombus in 96 percent of test rabbits.

The activity on the platelet stickiness was evidenced by the method of E. W. Salzman (J. Lab. Clin. Med. 62, 724 (1923)). It was found that the new compounds administered to the rabbit at 10 to 25 mg/kg I.V. and at 50 to 100 mg/kg P.O. decreases the platelet stickiness by 30 to 50%.

The new products have no notable effects on other blood cloting factors at the active dose on fibrinolysis and so do not provoke haemorrhage; they are effective by the oral route and so distinguish themselves from known enzymatic fibrinolytic substances, as streptokinase, urokinase and plasmin. To our knowledge, no oher synthetic chemical substance has this advantageous and safe activity and no similar product is at the present time on the pharmaceutical market. The mode of action seems to be the stimulation of the plasminogen proactivator, since the compounds have no effect on bovin plasma, which is devoid of proactivator.

The new products also inhibit in the rat the development of the ulcer of restraint (Method of S. Bonfils et al. Rev. Fr. Et. Clin. Biol. XI. 343 (1966)). At the dose of 2 to 200 mg/kg I.P., 25 to 75% of the animals are protected from ulceration, which occurs in 92% of the control animals.

An inhibition of the gastric secretion by the new products can also be observed by the method of H. Shay et al. (Gastroenterology 5, 43 (1945)). Doses of 10 to 150 mg/kg intraperitoneally decrease the hydrochloric acid ouput of the rat's stomach by 40 to 90%.

The low toxicity and the hereaove described pharmacological properties allow the use of the new products in therapy, especially in the prevention and the treatment of thrombosis, thromboembolic diseases, gastric ulcer and hypersecretion.

The present invention also provides pharmaceutical compositions containing a compound of the general formula (I) or a physiologically tolerable salt thereof, in admixture or conjunction with a suitable pharmaceutical carrier, such, for example, as distilled water, glucose, lactose, talc, starch, stearate of magnesium and cocoa butter. These pharmaceutical compositions may be in form of tablets, dragees, capsules, suppositories or solutions, in order to be administered by the oral, rectal or parenteral route, at doses of 5 to 500 mg 1 to 5 times a day.

The following Example illustrates such a pharmaceutical preparation:

Example 15

| (Tablets) | |
|---|---|
| Diethylammonium 2-hydroxy-5-(2-methyl thiazol-4-yl) benzoate | 100 mg |
| Lactose | 102 mg |
| Starch | 50 mg |
| Talc | 20 mg |
| Stearate of Magnesium | 3 mg |
| for 1 tablet to be drageified. | |

Using an effective amount of the new compounds, a human or animal being may successfully be prevented from thromboembolic disorders. The treatment may safely be continued over a long period of months or even years by the oral route, without notable side effects, such as haemorrhagic tendency, which is always the danger of the anticoagulants acting on other clotting factors.

Another advantage of the invention is the relatively low price of the compounds compared to the very expensive enzymatic substances, such as streptokinase.

we claim:

1. A method of treating a living animal body for alleviation of a diseased condition due to a thrombosis or a thromboembolism, comprising administering to said body orally, rectally, or parenterally compound selected from the group consisting of A. thiazolyl benzoic acid compounds of the general formula (I)

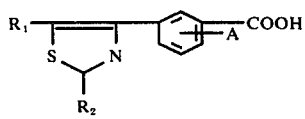

(I)

wherein:

R₁ and R₂ are selected from the group consisting of: lower alkyl containing 1 to 5 carbon atoms inclusive, phenylalkyl, phenyl, halophenyl, lower alkylphenyl, lower alkoxyphenyl and for $R_1$ hydrogen;

A is selected from the group consisting of: hydrogen, halogen, hydroxy, lower alkyl and lower alkoxy; and B. physiologically acceptable addition salts with mineral or organic bases, in an effective fibrinolytic amount.

2. Method of claim 1 wherein the compound is 2-hydroxy-5-(2-methyl thiazol-4-yl) benzoic acid, or a physiologically acceptable salt thereof.

3. Method of claim 1 wherein the compound is diethylammonium 2-hydroxy-5-(2-methyl thiazol-4-yl) benzoate.

4. Method of claim 1 wherein the compound employed is selected from the group consisting of:

A. 2-hydroxy-5-(2-phenyl thiazol-4-yl) benzoic acid,
2-methoxy-5-(2-methyl thiazol-4-yl) benzoic acid,
3-(2,5-dimethyl thiazol-4-yl) benzoic acid,
2-chloro-5-(2-methyl thiazol-4-yl) benzoic acid,
2-hydroxy-5-[2-(3,4-dimethoxyphenyl) thiazol-4-yl]benzoic acid,
2-methoxy-5-(2-phenyl thiazol-4-yl) benzoic acid,
3-(2-methyl thiazol-4-yl) benzoic acid
2-methoxy-5-(2-benzyl thiazol-4-yl) benzoic acid,
2-methyl-3-(2-isobutyl thiazol-4-yl) benzoic acid,
2-bromo-5-(2-ethyl-5-phenyl thiazol-4-yl) benzoic acid,
3-(2-methyl-5-paratolyl thiazol-4-yl)-4-ethoxy benzoic acid,
3-ethyl-5-(2-methyl-5-propyl thiazol-4-yl) benzoic acid,
3-(2-parachlorophenyl thiazol-4-yl) benzoic acid, and B. physiologically acceptable addition salts with mineral or organic bases.

5. Method of claim 1 wherein the compound is administered in an amount of 5 to 500 mg.

6. Method of claim 5 wherein the compound is administered 1 to 5 times a day.

7. A method of treating a patient for alleviation of a thrombosis or a thromboembolism which comprises administering to said patient orally, rectally, or parenterally, compound of the formula:

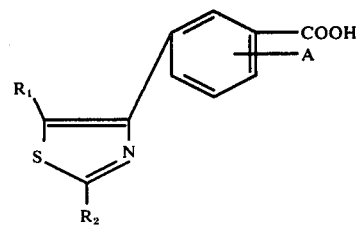

wherein:

$R_1$ is selected from the group consisting of hydrogen, lower alkyl having 1 to 5 carbon atoms inclusive, phenylalkyl, phenyl, halophenyl, loweralkylphenyl, and loweralkoxyphenyl, $R_2$ can have the same meaning as $R_1$ except for hydrogen, A is selected from the group consisting of hydrogen, halogen, hydroxy, loweralkyl, and loweralkoxy, in free or salified form with a mineral or organic base, in an effective fibrinolytic amount.

8. Parenteral pharmaceutical composition having fibrinolytic activity and useful for prevention or alleviation of a diseased condition due to a thrombosis or a thromboembolism, which contains as active fibrinolytic principle an effective amount of a compound selected from the group consisting of:

A. 2-hydroxy-5-(2-phenyl thiazol-4-yl) benzoic acid,
2-methoxy-5-(2-methyl thiazol-4-yl) benzoic acid,
3-(2,5-dimethyl thiazol-4-yl) benzoic acid,
2-chloro-5-(2-methyl thiazol-4-yl) benzoic acid,
2-hydroxy-5-[2-(3,4-dimethoxyphenyl) thiazol-4-yl] benzoic acid,
2-methoxy-5-(2-phenyl thiazol-4-yl) benzoic acid,
3-(2-methyl thiazol-4-yl) benzoic acid,
2-methoxy-5-(2-benzyl thiazol-4-yl) benzoic acid,
2-methyl-3-(2-isobutyl thiazol-4-yl) benzoic acid,
2-bromo-5-(2-ethyl-5-phenyl thiazol-4-yl) benzoic acid,
3-(2-methyl-5-paratolyl thiazol-4-yl)-4-ethoxy benzoic acid,
3-ethyl-5-(2-methyl-5-propylthiazol- 4-yl) benzoic acid,
3-(2-parachlorophenyl thiazol-4-yl) benzoic acid, and B. physiologically acceptable addition salts with mineral or organic bases.

9. Rectal pharmaceutical composition having fibrinolytic activity and useful for prevention or alleviation of a diseased condition due to a thrombosis or thromboembolism, which contains as active fibrinolytic principle an effective amount of a compound selected from the group consisting of:

A. 2-hydroxy-5-(2-phenyl thiazol-4-yl) benzoic acid,
2-methoxy-5-(2-methyl thiazol-4-yl) benzoic acid,
3-(2,5-dimethyl thiazol-4-yl) benzoic acid,
2-chloro-5-(2-methyl thiazol-4-yl) benzoic acid,
2-hydroxy-5-[2-(3,4-dimethoxyphenyl) thiazol-4-yl] benzoic acid,
2-methoxy-5-(2-phenyl thiazol-4-yl) benzoic acid,
3-(2-methyl thiazol-4-yl) benzoic acid,
2-methoxy-5-(2-benzyl thiazol-4-yl) benzoic acid,
2-methyl-3-(2-isobutyl thiazol-4-yl) benzoic acid,
2-bromo-5-(2-ethyl-5-phenyl thiazol-4-yl) benzoic acid,
3-(2-methyl-5-paratolyl thiazol-4-yl)-4-ethoxy benzoic acid,
3-ethyl-5-(2-methyl-5-propyl thiazol-4-yl) benzoic acid,
3-(2-parachlorophenyl thiazol-4-yl) benzoic acid, and B. physiologically acceptable addition salts with mineral or organic bases.

* * * * *